United States Patent [19]

Quiring et al.

[11] 4,134,935

[45] Jan. 16, 1979

[54] DENTAL VARNISHES

[75] Inventors: Bernd Quiring, Leverkusen; Kuno Wagner, Leverkusen-Steinbuchel; Joachim König, Schildgen, all of Germany

[73] Assignee: Bayer Aktiengesellschaft, Germany

[21] Appl. No.: 702,904

[22] Filed: Jul. 6, 1976

Related U.S. Application Data

[63] Continuation of Ser. No. 277,804, Aug. 3, 1972, abandoned.

[30] Foreign Application Priority Data

Aug. 12, 1971 [DE] Fed. Rep. of Germany ....... 2140404

[51] Int. Cl.² ............................................. C08L 75/00
[52] U.S. Cl. ............................ 260/859 R; 260/998.11; 260/DIG. 36
[58] Field of Search ............................ 260/859, 859 R

[56] References Cited

U.S. PATENT DOCUMENTS

| | | | |
|---|---|---|---|
| 3,457,326 | 7/1969 | Kienle | 260/859 |
| 3,509,234 | 4/1970 | Burlant | 260/859 |
| 3,531,364 | 9/1970 | Schmidle | 260/859 |
| 3,607,973 | 9/1971 | Holicky | 260/859 |
| 3,607,974 | 9/1971 | Holicky | 260/859 |
| 3,632,789 | 1/1972 | Wilhelm | 260/859 |
| 3,632,796 | 1/1972 | Holicky | 260/859 |
| 3,641,199 | 2/1972 | Niederhauser | 260/859 |
| 3,677,920 | 7/1972 | Kai | 260/859 |
| 3,690,946 | 9/1972 | Hartmann | 260/859 |
| 3,719,638 | 2/1973 | Huemmer | 260/859 |

*Primary Examiner*—Paul Lieberman
*Attorney, Agent, or Firm*—Jacobs & Jacobs

[57] ABSTRACT

Graft copolymers or telomerisates made of polyisocyanates and a copolymer of methylmethacrylate bearing isocyanategroups or groups reactive with isocyanates can be employed as dental varnishes. They demonstrate high abrasion resistance, are quick drying and hardening, and possess excellent adhesion properties.

13 Claims, No Drawings

DENTAL VARNISHES

CROSS-REFERENCE

This is a continuation of Ser. No. 277,804 filed Aug. 3, 1972, now abandoned.

The present invention relates to varnishes especially prepared for use in dentistry as cavity lines and fissure sealants. Thus they are applied in a dental cavity prior to the introduction of the filling materials, thereby protecting the dental pulp and preventing the development of edge cracks between tooth and filling material. As fissure sealants they seal the tooth surfaces and deeper fissures, forming a highly adhesive protective layer and protecting the tooth from salivary attack.

It is known that dental varnishes are capable of reducing the susceptibility of the tooth to caries attack. Such varnishes include two-component systems consisting of methyl cyanoacrylate and filling materials, and diisocyanates and polyols, in which the two components are mixed and then applied to the tooth material; see, e.g., J. Am. Dent. Assoc. 75:121, 1967. Systems have also been described in which a polymerizable monomer mixture consisting of bisphenol A - glycidyl methacrylate and methyl methacrylate are applied to the enamel. Such systems are hardened by means of UV radiation; see, e.g., J. Am. Dent. Assoc. 80:324, 1970.

Such systems pose a number of disadvantages. The individual components often present biological risks. The former type of system also requires that the two components be mixed prior to use and then used very quickly, the shelf-life of the mixture being very short. The latter system is time-consuming since hardening of the applied varnish is effected by means of UV radiation. The known systems display poor abrasion resistance and inferior adhesion to tooth material. For this reason the enamel retains the varnish for only a short time. The varnish must thus be frequently reapplied to obtain lasting protection against caries.

It has now been found that the graft copolymers of the present invention can be employed in the preparation of dental varnishes which excel all other systems hitherto known to the art. Particularly notable characteristics of the resultant varnish are high abrasion resistance and firm adhesion to the tooth substance. A further advantage of particular importance for dental use is the short drying and hardening time of these varnishes, which can be adjusted by means of catalysts and the solvent. These graft copolymers themselves, which can be prepared as described in German Offenlegungsschrift No. 2,031,408, comprise (1) from about 10 to about 95% by weight of a polyisocyanate, said polyisocyanate being grafted to a methacrylic copolymer of (2)
 (a) from about 5 to about 70% by weight of methyl methacrylate,
 (b) from about 0.3 to about 10% by weight of at least one olefinic comonomer bearing a bridging member selected from an isocyanate group and a group capable of reacting with isocyanate groups, and
 (c) from 0 to about 25% by weight of olefinic comonomer;

Particularly preferred are graft copolymers prepared from 30 to 85 percent by weight of at least one aliphatic or araliphatic polyisocyanates, 15 to 55 percent by weight of methyl methacrylate, 1 to 5 percent by weight of unsaturated olefinic compounds containing either at least one group which reacts with an isocyanate or at least one isocyanate group in the molecule, and up to 10 percent by weight of other unsaturated olefinic compounds.

The graft copolymers prepared according to the invention and containing isocyanate groups may be used in one component air drying varnishes, either in bulk form or in solution. Alternatively they can be employed in two-component varnishes by combining them with a second component capable of reacting with isocyanate. Finally they can be used in the form of separable varnishes with blocked isocyanate groups.

The polyisocyanates used to prepare these graft copolymers can be aliphatic, cycloaliphatic and araliphatic polyisocyanates. In each case the carbon atoms adjacent to the isocyanate groups will bear at least one hydrogen atom, preferably two, and will not be aromatic. The remainder of the molecule may be composed of alkane, cycloalkane, or phenyl structures, or combinations thereof. Thus included are alkane diisocyanates such as 1,3-trimethylene diisocyanate, 1,4-tetramethylene diisocyanate, 1,5-pentamethylene diisocyanate, 1,6-hexamethylene diisocyanate, 2,2,4-trimethyl-1,6-diisocyanatohexane, 2,4,4-trimethyl-1,6-diisocyanatohexane, dodecamethylene diisocyanate, and the like; cycloalkane diisocyanates such as 1,2-diisocyanatocyclobutane, dicyclohexyl-4,4'-diisocyanate, dicyclohexylmethane-4,4'-diisocyanate, 1-methyl-2,4-diisocyanatocyclohexane, 1-methyl-2,6-diisocyanatocyclohexane, isophorone diisocyanate and the like; diisocyanates containing aromatic groups such as m- and p-xylylene diisocyanate; esters such as α,ε-diisocyanatocaproic acid alkyl esters with 1 to 8 carbon atoms in the alcohol group; and triisocyanates such as biuret triisocyanates, which can be prepared according to German Pat. No. 1,101,394. In addition to the above type of di- and triisocyanates, one can also employ adducts of diisocyanates with di- and/or polyhydric alcohols, amines, carboxylic acids, and mercaptans. These include the reaction product of 2 moles of diisocyanate and 1 mole of a difunctional compound such as ethylene glycol, 1,2-propanediol, 2,2-dimethyl-1,3-propanediol, 1,3-butanediol, 1,4-butanediol, 2-ethyl-1,3-hexanediol, N-methyldiethanolamine, N-methyldipropanolamine, 2-methylaminoethanol, N-(2-hydroxyethyl)-cyclohexylamine, 1-cyclohexylamino-2-propanol and the like, as well as the reaction product of 3 moles of diisocyanate and 1 mole of a di- or trifunctional compound such as trimethylolpropane, glycerol, aminoethanol, diethanolamine, triethanolamine, 3-amino-1-propanol, N-cyclohexyltrimethylenediamine. Moreover these adducts include those di- and triisocyanates with higher molecular weight polyols, polyamines, polycarboxylic acids, and polyesters, including polyether polyols, polymers containing functional amino groups, polymers containing hydroxyl- and/or carboxyl groups and the like; in short, any stable polymer having pendant or terminal groups capable of reacting with isocyanate. In this case, at least 0.8 mole of diisocyanate is used per gram equivalent of the functional groups.

Preferred polyisocyanates include 4,4'-diisocyanato dicyclohexylmethane, triisocyanatohexyl biuret, dicyclohexyl-4,4'-diisocyanate, m-xylylene diisocyanate, isophorone diisocyanate, hexamethylene diisocyanate, 2,2,4- and 2,4,4-trimethylhexamethylene 1,6-diisocyanate, and α,ε-diisocyanatocaproic acid esters with alcohols containing 1 to 8 carbon atoms, as well as adducts thereof with ethylene glycol, 1,2-propanediol, 1,3- butanediol, 1,4-butanediol, 2,2-dimethyl-1,3-propanediol, trimethylolpropane, glycerol, and higher molecular weight polyesters having terminal hydroxy groups.

The side chain of the graft copolymers of this invention is a copolymer made of methylmethacrylate and a comonomer with at least one unsaturated olefinic group containing isocyanate groups or groups capable of reacting with isocyanate groups and if necessary further unsaturated olefinic comonomers.

Any unsaturated olefinic compound which enters into a methacrylate copolymerization and further bears a group which enters into an isocyanate reaction may be employed as comonomer. Such groups include the isocyanate group itself and groups capable of reacting with isocyanate such as hydroxy, mercapto, amino, carboxy and epoxide. Typical comonomers include allyl alcohol, hydroxy alkyl esters of acrylic or methacrylic acid, the corresponding glycidyl esters, monoesters of maleic or itaconic acid, dihydroxy diesters of maleic or itaconic acid, allylamine, acrylamide, methacrylamide, acrylic acid, methacrylic acid, N-methylolacryl- and methacrylamide, isocyanatoalkyl methacrylate, vinyl isocyanate and allyl isocyanate, butadiene monoxide. The alkyl groups will generally have up to 6 carbon atoms. Preferred comonomers are $\beta$-hydroxyethyl acrylate, $\beta$-hydroxypropyl acrylate, $\beta$-hydroxyethyl methacrylate, $\beta$-hydroxypropyl methacrylate, acrylic acid, methacrylic acid, and $\beta$-isocyanatoethyl methacrylate.

In the synthesis of these graft copolymers, the unsaturated olefinic compounds containing isocyanate groups or groups capable of reacting with isocyanate groups are used in amounts of from about 0.3 to about 10 percent by weight. In using unsaturated olefinic compounds containing groups capable of reacting with isocyanate groups, the amount of the comonomer should be such that during the preparation of the graft copolymers and their subsequent storage, the partial reaction which occurs between the free isocyanate groups of the graft polymers and the pendant groups does not lead to excessive cross-linking. Attention to this will ensure that in every case the products are readily soluble in the varnish solvent such as xylene, toluene, ethyl glycol ether acetate, butyl acetate, methylene chloride or chloroform.

In addition a second comonomer can be employed. These are simply unsaturated olefinic compounds known to be copolymerizable with methyl-methacrylate and are optionally used in amounts up to about 25 percent by weight as conventional methacrylate comonomers. These include olefins containing 2 to 6 carbon atoms such as ethylene, propylene, butadiene, isoprene, dimethylbutadiene, 2-chlorobutadiene, and 2,3-dichlorobutadiene; alkyl esters of acrylic acid or methacrylic acid, and alcohols containing up to 18, preferably up to 8 carbon atoms, such as methyl acrylate, ethyl acrylate, butyl methacrylate, octyl acrylate, octyl methacrylate and the like; vinyl compounds such as vinyl esters, vinyl chloride, vinylidene chloride, methyl vinyl sulfone, N-vinylpyrrolidone, styrene, $\alpha$-methylstyrene, methyl vinyl ketone; nitriles such as acrylonitrile and methacrylonitrile; dialkylesters of maleic or itaconic acid; N-methylolalkyl ethers of acrylamide or methacrylamide, particularly the N-methylolmethyl ethers; as well as the reaction products of methoxymethyl isocyanate and $\beta$-hydroxyethyl acrylate, $\beta$-hydroxypropyl acrylate, $\beta$-hydroxyethyl methacrylate and $\beta$-hydroxypropyl methacrylate. Particularly preferred are the acrylic acid esters containing up to 18, preferably 8 carbon atoms, in the alcohol groups, such as methyl-, ethyl-, propyl-, butyl-, octyl acrylate; and methacrylic acid esters containing 2 to 18, preferably up to 8 carbon atoms, in the alcohol group, such as ethyl-, propyl-, butyl-, or octyl methacrylate, as well as vinyl acetate, acrylonitrile and styrene.

The graft copolymers according to the invention may be prepared by bulk or solution polymerization as described for example in Belgian Pat. No. 723,640. The graft copolymers can be prepared as well as used in conventional solvents such as benzene, toluene, xylene, chlorobenzene, o-dichlorobenzene, butyl acetate, ethyl glycol ether acetate, methyl isobutyl ketone, cyclohexanone, methylene chloride, chloroform, carbon tetrachloride, as well as mixtures thereof.

The graft copolymerization itself can be carried out by dropwise addition of the monomer or monomer mixture to, or by passing the monomer or monomer mixture through, the polyisocyanate in the presence of free radicals at temperatures of 15 to 150° C, preferably 50 to 140° C. In general, the process is carried out at the higher end of the temperature range for purposes of yield but it is also practical to operate at or near room temperature. The grafting reaction can be conducted simultaneously or subsequently through the use of radical generating agents, heat, radiation, (alone or in combination with photoactivating agents), or combinations thereof.

The graft copolymers obtained are substantially non-cross-linked, readily soluble products with molecular weights ranging from about 600 to about 12,000, more generally 800 to 10,000. They contain a high proportion of isocyanate groups, so that they are amenable to numerous well-known conversion reactions utilizing this group. Various advantages and special effects can thus be achieved by reacting the grafted polyisocyanates with isocyanate reactive compounds in small quantities that are insufficient to cause the complete cross-linking or undesirable reaction with the polyisocyanates. Thus, reaction with a small amount of a polyester with a molecular weight of 2000 made of adipic acid and ethylene glycol containing terminal OH groups, results in the elastification of the films, while the reaction with a small amount of a branched polyester prepared from 5 moles of phthalic acid, 1 mole of trimethylolpropane, 2,5 moles of 1,3-butanediol and 2.5 moles of 2,2-bis-(4-hydroxycyclohexyl) propane containing 2% OH causes an additional acceleration of the drying of the films.

As previously observed these graft copolymers can be employed in a number of ways. They can be used in the preparation of one-component varnishes which harden simply by reaction with atmospheric humidity. They can also be used in two-component varnishes in which the second component is a compound containing isocyanate reactive groups such as hydroxy, mercapto, amino or carboxy, which optionally may be formed only during the hardening process. Particularly preferred reaction partners for such systems include polyamines (which can be present in the form of the corresponding polyketimines) such as ethylenediamine, triethylenetetramine, tetraethylenepentamine, dipropylenetriamine, tripropylenetetramine, N-methylpropylenediamine, hexamethylenediamine, N,N'-biscyclohexyl-m-xylylenediamine, N,N'-biscyclohexylisophoronediamine and the like; the hydrogenated addition products of 2 moles of acrylonitrile with ethylamine, propylamine, ethylenediamine and the like, the hydrogenated addition products of x moles of acrylonitrile with polyols, where x represents the number of hydroxyl equivalents; polyethers, polyesters and polymers containing hydroxyl- and/or carboxyl groups such as polyethylene oxides, polypropylene oxides, polybutylene oxides, polytetrahydrofuranes containing 2 to 6 hydroxyl groups and copolymers thereof; polyacetals containing carboxyl- and/or hydroxyl groups; polyesters of carbonic acid, adipic acid, phthalic acid, tetrahydrophthalic acid, hexahydrophthalic acid, endomethylenetetrahydrophthalic acid and methylhexahydrophthalic acid with di- and/or polyhydric alcohols such as ethylene glycol, diethylene glycol, triethylene glycol, octaethylene glycol, 1,2-propyleneglycol, polypropylene glycol, 2,2-dimethyl-1,3-propanediol, 1,3-butanediol, 1,4-butanediol, 2,2-bis-(4-hydroxycyclohexyl)propane, 2,2-bis-(4-hydroxyphenyl)propane, trimethylolpropane, glycerol and the like; hydroxyl- and/or carboxyl containing copolymers of unsaturated olefinic monomers such as styrene, alkyl acrylates with 1 to 8 carbon atoms in the alkyl group, acrylonitrile, ethylene, vinyl chloride, vinyl acetate, allyl alcohol, vinyl alcohol, hydroxyethyl- and hydroxypropyl esters of acrylic and methacrylic acid, acrylic acid, methacrylic acid, maleic acid, fumaric acid, maleic acid monoesters and the like.

In this reaction the quantitative ratio between the graft copolymer and the isocyanate reaction partner is generally chosen in such a way that up to three, but preferably one hydroxyl, amino, mercapto and/or carboxyl group is present per free isocyanate group.

To accelerate hardening of the graft copolymer, catalysts customarily used in isocyanate chemistry may be used. These include tertiary amines such as triethylamine, pyridine, methylpyridine, benzyldimethylamine, N,N-dimethylaminocyclohexane, N-methylpiperidine, pentamethyldiethylenetriamine, N,N'-endoethylenepiperazine, N,N'-dimethylpiperazine, 1,5-diazabicycloundecene and the like; metal salts such as iron(III) chloride, zinc chloride, zinc 2-ethylcaproate, tin(II) 2-ethylcaproate, dibutyltin (IV) dilaurate, dioctyltin(IV) dilaurate, tin octoate, molybdenum glycolate, and the like;

If necessary, the grafted polyisocyanate, the polyfunctional reaction partner and/or the catalyst and additives are thoroughly mixed in solution or in bulk form prior to their application to the surface to be varnished. In the bulk form, it is expedient to carry out the mixing in the melt, in order to obtain a homogeneous mass.

The varnishes prepared according to the invention may be applied to the tooth substance in liquid form, e.g. in the form of a solution or from the melt. They produce clear films on the enamel with an esthetic appearance; adhere surprisingly well to the tooth substance even in the moist oral environment; are particularly light-fast; possess a high degree of color stability and resistance to abrasion; and dry and harden even at low temperatures. The drying and hardening times can be further reduced through the application of a stream of air. These films are characterized by great hardness, elasticity, high gloss and great resistance to salivary action. In addition, they may contain pigments or anticarious additives such as titanium dioxide, quartz, silicates, calcium hydroxyl apatite, calcium phosphate and fluoride, sodium phosphate and fluoride, disodium-monofluorophosphate, and aluminum fluoride.

One useful embodiment of the present invention pertains to dental varnishes ready for application and comprising a substantially moisture free solution of at least one graft copolymer of the present invention in a volatile organic solvent therefore. Such solvents include esters such as ethyl acetate, ethyl glycol ether acetate, butyl acetate and the like; halogenated alkanes such as methylene chloride and chloroform, and hydrocarbons such as xylene and toluene, as well as mixtures thereof.

The following examples will serve to further typify the nature of the invention but should not be considered as a limitation on the scope thereof. The parts referred to in the following examples refer to parts by weight, unless otherwise specified.

EXAMPLE 1

A flask, equipped with reflux condenser, stirrer, thermometer, nitrogen delivery tube and a dropping funnel, is cooled to 12 to 14° C, and a solution of 225 parts of technical triisocyanatohexyl biuret (having an isocyanate content of about 22%) in 617 parts of xylene is added and heated to 120° C under nitrogen, with the exclusion of moisture. At this temperature, a mixture of 180 parts of methyl methacrylate, 6 parts of β-hydroxypropyl methacrylate and 2.2 parts of azobisisobutyronitrile is added dropwise over a period of 3¼ hours. The mixture is then stirred for 20 minutes and a clear, approximately 40% solution of low viscosity is obtained with an isocyanate content of 4.6%. This solution is stirred with a solution of 13.2 parts of a linear polyester of adipic acid and ethylene glycol having an OH content of 1.7% in 20.4 parts of a mixture of equal parts of ethyl glycol ether acetate and xylene, also in the absence of moisture, until a constant isocyanate content is obtained. The solvent is removed at temperatures of up to 100° C under vacuum and the residue is dissolved in sufficient chloroform to yield a 15% solution. This is treated with 0.1% of dibutyltin dilaurate, calculated on the solution. The resulting solution of low viscosity has an isocyanate content of 1.7% and is designated as varnish A.

EXAMPLE 2

A mixture of 225 parts of technical triisocyanatohexyl biuret and 6.3 parts of a linear polyester having terminal hydroxyl groups (prepared from adipic acid, ethylene glycol and 1,4-butanediol) in 363 parts of xylene is heated to 120° C under nitrogen and in the absence of moisture. A mixture of 180 parts of methyl methacrylate, 6 parts of β-hydroxypropyl methacrylate and 2.2 parts of diethyl azodiisobutyrate, cooled to 12–14° C, is dropwise added over a period of 4-½ hours and the reaction mixture is then stirred for 30 minutes. The solvent is removed by vacuum distillation at 100° C. The residue, which is sticky at room temperature and has an isocyanate content of 11–12%, is dissolved in methylene chloride to a concentration of 17% and treated with 0.1% dioctyltin laurate, calculated on the solution. It is designated as varnish B.

EXAMPLE 3

By treating 100 parts of varnish B with 1,8 parts of sodium fluoride, a further product, designated as varnish C, is obtained.

The graft copolymer used in preparing varnish B is alternatively dissolved in a 90:10 mixture of methylene chloride and ethyl glycol ether acetate to a concentration of 14% and treated with 0.1% dibutyltin dilaurate. The resulting product is designated as varnish D.

EXAMPLE 4

In the apparatus described in Example 1, a mixture of 50 parts of methyl methacrylate, 10 parts of butyl acrylate, 2 parts of β-hydroxypropyl methacrylate and 0.7 part of azobisisobutyronitrile, cooled to 12–14° C, is added dropwise to a solution of 75 parts of technical triisocyanatohexyl biuret in 206 parts of xylene over a 3-hour period at 120° C, under nitrogen and in the absence of moisture. The reaction mixture is stirred for 30 minutes at this temperature. After addition of a solution of 8.8 parts of a linear polyester of adipic acid and ethylene glycol (an OH content of 1.7%) in 13.5 parts of xylene, the mixture is stirred at 90° C until the isocyanate content is decreased to 3.8%. The product is freed from solvent at temperatures of up to 100° C by vacuum distillation and dissolved in chloroform to yield a 51% solution having an isocyanate content of 5.5%, to which is added 0.2% dibutyltin(IV) dilaurate, calculated on the solid resin portion. The product is designated as varnish E.

EXAMPLE 5

The following materials are employed in the procedure of Example 1:
75 parts of triisocyanatohexyl biuret (tech.)
205 parts of a mixture of equal parts of ethyl glycol ether acetate and xylene
60 parts of methyl methacrylate
1 part of acrylic acid
0.7 part of α,α'-azobisisobutyronitrile.
The product is a clear yellow, approximately 40% solution of low viscosity with an isocyanate content of 5%.
Varnish F is obtained through dilution of this product with the same solvent system to a concentration of 20% and addition of 0.1% dibutyltin dilaurate.

EXAMPLE 6

The procedure described for Example 1 is used, with the following quantities of reactants:
75 parts of technical triisocyanatohexyl biuret
186 parts of a 1:1 mixture of ethyl glycol ether acetate and xylene
60 parts of methyl methacrylate
2.2 parts of β-isocyanatoethyl methacrylate
0.75 parts of α,α'-azobisisobutyronitrile
20 parts of carbon tetrachloride.
70 parts of distillate are collected in vacuo and replaced by a 1:1 mixture of ethyl glycol ether acetate and xylene. A solution of 4:4 parts of the linear polyester prepared from adipic acid and ethylene glycol with an OH content of 1.7%, in 6.6 parts of the same solvent mixture, is added and stirred for 3 hours at 90° C in the absence of moisture.
The product is a clear yellow, approximately 40% solution of low viscosity with an isocyanate content of 4.8%. By adding 0.25% dibutyltin dilaurate and diluting to a concentration of 20%, varnish G is obtained.

EXAMPLE 7

Utilizing apparatus equivalent to that described in Example 1, a mixture of 26 parts of 2,2-dimethyl-1,3-propanediol and 22.5 parts of trimethylolpropane is added in portions over a 3-hour period to a solution of 222 parts of isophorone diisocyanate in 183 parts of a 1:1 mixture of ethyl glycol ether acetate and xylene at 80–85° C in the absence of moisture. The reaction mixture is then stirred at the same temperature for 3 hours, diluted with 212 parts of a 1:1 mixture of ethyl glycol ether acetate and xylene, and treated dropwise over a 3-hour period at 120° C, under nitrogen and in the absence of moisture, with a mixture of 100 parts of methyl methacrylate, 15 parts of β-hydroxypropyl methacrylate and 1.5 parts of α,α'-azobisisobutyronitrile. The mixture is stirred at the same temperature for an additional hour. The solvent is then distilled off in vacuo and the residue dissolved in methylene chloride to form a 25% solution. The product is a clear colorless solution of low viscosity, with an isocyanate of 2.5%. A sprayable varnish, designated as varnish H, is obtained through addition of 1% endoethylenepiperazine.

EXAMPLE 8

The same procedure is used as in Example 7, with the following quantities of reactants: 168 parts of hexamethylene diisocyanate in 183 parts of a 1:1 mixture of ethyl glycol ether acetate and xylene; 7.5 parts of trimethylolpropane and 43.6 parts of 2,2-dimethyl-1,3-propanediol in 145 parts of a 1:1 mixture of ethyl glycol ether acetate and xylene; and 120 parts of methyl methacrylate, 5 parts of β-hydroxypropyl methacrylate, and 2 parts of α,α'-azobisisobutyronitrile in 188 parts of a 1:1 mixture of ethyl Glycol ether acetate and xylene. The reaction product is a yellow, slightly turbid, aproximately 40% solution of low viscosity with an isocyanate content of 3.2%. By distilling off the solvent in a vacuum, dissolving the residue in ethyl acetate, diluting to 25% and adding 0.1% dibutyltin dilaurate, a product designated as varnish J is obtained.

EXAMPLE 9

The same procedure is used as in Example 7, with the following quantities of reactants: 188 parts of m-xylylene diisocyanate in 183 parts of a 1:1 mixture of ethyl glycol acetate and xylene; 26 parts of 2,2-dimethyl-1,3-propanediol and 22.5 parts of trimethylolpropane in 162 parts of a 1:1 mixture of ethyl glycol ether acetate and xylene; and 120 parts of methyl methacrylate, 5 parts of β-hydroxypropyl methacrylate and 2 parts of α,α'-azobisisobutyronitrile in 172 parts of a 1:1 mixture of ethyl glycol ether acetate and xylene. A slightly turbid yellow, approximately 40% solution of low viscosity is thus obtained with an isocyanate content 2.8%. By diluting with a 1:1 mixture of ethyl glycol ether acetate and xylene to a solid content of 20%, and adding 0.1% dibutyltin (IV) dilaurate, calculated on the solution, a product designated as varnish K is obtained.

EXAMPLE 10

The procedure escribed for Example 1 is used, with the following quantities of reactants: 75 parts of 4,4'-diisocyanatodicyclohexylmethane in 222 parts of a 1:1 mixture of ethyl glycol ether acetate and xylene; 60 parts of methyl methacrylate; 12 parts of β-hydroxypropyl methacrylate; and 1 part os α,α'-azobisisobutyronitrile. A clear yellow solution of low viscosity is obtained with an isocyanate content of 5.2%. The product is diluted with the same solvent mixture to a solid content of 20% and treated with 0.1% dibutyltin dilaurate (varnish L).

EXAMPLE 11

The following tests demonstrate the superior drying and hardening rates of the present varnishes.
The varnish is placed on a cleaned glass plate between two tin foils and flattened out. Emery dust is sprinkled on the varnish at 10-second intervals, and then blown away. The end of the drying period is reached when about 95% of the emery powder can be blown away.

Afterwards, the hardness of the varnish is continuously tested by means of a hardness-testing rod of Erichsen Co. (spring thickness 0.6 mm; initial load 250 g). The hardening time is defined as the time at which the engraving point of the hardness testing rod leaves a just barely visible trace when the rod is drawn over the surface of the varnish.

Table I

| Varnish | Drying Time (Sec.) | Hardening Time (Min.) |
|---|---|---|
| A | 70 | 30 |
| B | 70 | 20 |
| C | 100 | 25 |
| D | 240 | 25 |
| X* | 900 | 25 |

*A commercial dental varnish derived from 4,4'-diphenylmethanediisocyanate and polybutadienediol

EXAMPLE 12

The following demonstrates the abrasive resistance of these varnishes.

The varnish is applied to a thoroughly cleaned glass plate 6 times at 3-minute intervals, and dried in air. After 30 minutes from the first application, the coated plate is placed into de-ionized water and stored for about 16 hours at 37° C. After careful drying and weighing, the varnish (approximate 380 mg) layer is subjected to abrasion consisting of 50,000 brushing movements with a standardized tooth brush (load 1.5 kg) and tooth paste. After the test, the glass plate is cleaned, dried and weighed.

Table II

| Varnish | Weight Loss (mg) |
|---|---|
| A | 6.8 |
| B | 3.7 |
| X | 21.2 |

EXAMPLE 13

The following demonstrates the adhesion strength of these varnishes after exposure to water.

Freshly extracted calves' teeth are stored in water for 1–10 days, then inbedded in an autopolymer and surfaceground with a diamonded wheel. The enamel surface is cleaned with an acid solution, rinsed with water and dried. The varnish solution is applied and dried for 3 minutes in a stream of cold air. A cylindrical ring is placed on the surface of the varnish and filled with cold-setting filling material containing polymethyl methacrylate and methyl methacrylate, together with a support for stripping tests, which is allowed to harden. After polymerization of this filling material, the samples are stored in water at 37° C and then the adhesive strength is measured by means of a stripping machine at 16 hours, 7 days and 6 weeks. The following results representing average values of three individual measurements were thus obtained.

Table III

| Varnish | Adhesive Strength (kg/cm$^2$) | | |
|---|---|---|---|
| | 16 hours | 7 days | 6 weeks |
| A | 77 | 53 | 41 |
| B | 170 | 75 | 58 |
| C | 131 | 86 | 60 |
| D | 149 | 105 | 64 |
| E | 58 | 40 | — |
| X | 31 | 28 | 5 |

What is claimed is:

1. A graft copolymer or telomerisate of
(1) from about 10 to 95% by weight, based on the weight of the graft copolymer, of a polyisocyanate, and
(2) a copolymer of:
   (a) from about 5 to about 70% by weight, based on the weight of the graft copolymer, of methyl methacrylate,
   (b) from about 0.3 to about 10% by weight, based on the weight of the graft copolymer, of at least one olefinic comonomer bearing a bridging member selected from an isocyanate group and a group capable of reacting with isocyanate groups, and
   (c) from 0 to about 25% by weight, based on the weight of the graft copolymer, of an olefinic comonomer, said graft copolymer having a free isocyanate content of 7% to 12.5% by weight.

2. The graft copolymer according to claim 1, having a molecular weight of from about 600 to about 12,000, being substantially non-crosslinked and soluble in organic solvents and having a free isocyanate content in the range of from about 7% to about 12.5%.

3. A graft copolymer as defined in claim 1 wherein said polyisocyanate is formed from the reaction of di- or triisocyanate and at least one polyol.

4. A graft copolymer as defined in claim 1 wherein said polyisocyanate is a block copolymer formed from a di- or triisocyanate and a polymer containing free hydroxy, amino or carboxy groups.

5. A graft copolymer as defined in claim 1 wherein said graft polymer has a molecular weight of from about 800 to about 10,000.

6. A graft copolymer as defined in claim 5 wherein
(1) said methacrylate is derived from the polymerization of
   (a) from about 15 to about 55% by weight of methyl methacrylate,
   (b) from about 1 to about 55 by weight of an olefinic comonomer bearing a bridging member selected from the group consisting of isocyanate, hydroxy, mercapto, amino, carboxy or epoxy, and
   (c) from 0 to 10% of olefinic comonomer; and
(2) said polyisocyanate is present in an amount of from about 30 to about 85% by weight.

7. A graft copolymer as defined in claim 6 wherein the polyisocyanate is an adduct formed from the reaction of a trialkylbiuret triisocyanate, alkylene diisocyanate, cycloalkyl diisocyanate, dicycloalkylalkyl diisocyanate, or phenylene dialkyl diisocyanate and a polyol.

8. A graft copolymer as defined in claim 7 wherein the polyol is a straight or branched chain alkane diol or alkane triol having up to 6 carbon atoms.

9. A graft copolymer as defined in claim 7 wherein the polyol is a polyester having terminal hydroxy groups.

10. A graft copolymer as defined in claim 9 wherein the polyester is prepared from adipic acid and at least one alkane diol having up to 6 carbon atoms.

11. A graft copolymer as defined in claim 10 wherein at least one of the alkane diols is ethylene glycol.

12. A graft copolymer as defined in claim 6 wherein said bridging comonomer is selected from the group consisting of acrylic acid, methacrylic acid, hydroxy(-lower alkyl) esters of acrylic acid and methacrylic acid, and isocyanato(lower alkyl) esters of acrylic acid and methacrylic acid.

13. A dental varnish in a liquid form for application to dental surfaces comprising a graft copolymer as defined in claim 1 in solution with an inert volatile organic solvent substantially free of moisture.

* * * * *